United States Patent
Lachner et al.

(10) Patent No.: US 10,610,124 B2
(45) Date of Patent: Apr. 7, 2020

(54) LOCALIZATION OF FIBROUS NEURAL STRUCTURES

(75) Inventors: Rainer Lachner, Munich (DE); Andreas Blumhofer, Munich (DE)

(73) Assignee: Brainlab AG, Munich (DE)

(*) Notice: Subject to any disclaimer, the term of this patent is extended or adjusted under 35 U.S.C. 154(b) by 1378 days.

(21) Appl. No.: 14/419,961

(22) PCT Filed: Aug. 9, 2012

(86) PCT No.: PCT/EP2012/065567
§ 371 (c)(1),
(2), (4) Date: Feb. 6, 2015

(87) PCT Pub. No.: WO2014/023350
PCT Pub. Date: Feb. 13, 2014

(65) Prior Publication Data
US 2015/0164366 A1 Jun. 18, 2015

(51) Int. Cl.
| A61B 5/055 | (2006.01) |
| G06T 7/11 | (2017.01) |
| A61B 5/00 | (2006.01) |
| G06F 19/00 | (2018.01) |

(52) U.S. Cl.
CPC ............ *A61B 5/055* (2013.01); *A61B 5/4893* (2013.01); *A61B 5/7275* (2013.01); *G06F 19/34* (2013.01); *G06T 7/11* (2017.01); *G06T 2207/10092* (2013.01); *G06T 2207/20128* (2013.01); *G06T 2207/30016* (2013.01)

(58) Field of Classification Search
CPC ...... A61B 5/055; A61B 5/4893; A61B 5/7275; G06T 7/11; G06T 2207/10092; G06T 2207/30016; G06T 2207/20128; G06F 19/34
See application file for complete search history.

(56) References Cited

U.S. PATENT DOCUMENTS

2006/0229856 A1* 10/2006 Burrus ............ G01R 33/56341
703/11

OTHER PUBLICATIONS

Barbieri, Atlas-based fiber reconstruction from diffusion tensor MRI data, Int J Cars (2012) 7:959-967.*

(Continued)

*Primary Examiner* — Boniface N Nganga
(74) *Attorney, Agent, or Firm* — Tucker Ellis LLP

(57) ABSTRACT

A data processing method for determining a path of a neural fibre in a patient, comprising the steps of:
a) acquiring an atlas dataset representing an atlas of a fibrous structure comprising the neural fibre
b) acquiring a nerve indicating dataset comprising information suitable for identifying the neural fibre in the patient
c) calculating a matched atlas dataset by registering the atlas dataset with the nerve indicating dataset
d) obtaining a generic path of the neural fibre from the matched atlas dataset
e) defining a constraining volume in the patient around the generic path, the constraining volume having at least two end surfaces on which the generic path ends and
f) determining the path of the neural fibre between end surfaces using a probabilistic approach, wherein the determined path lies completely within the constraining volume.

18 Claims, 7 Drawing Sheets

(56) References Cited

OTHER PUBLICATIONS

Figure 1:
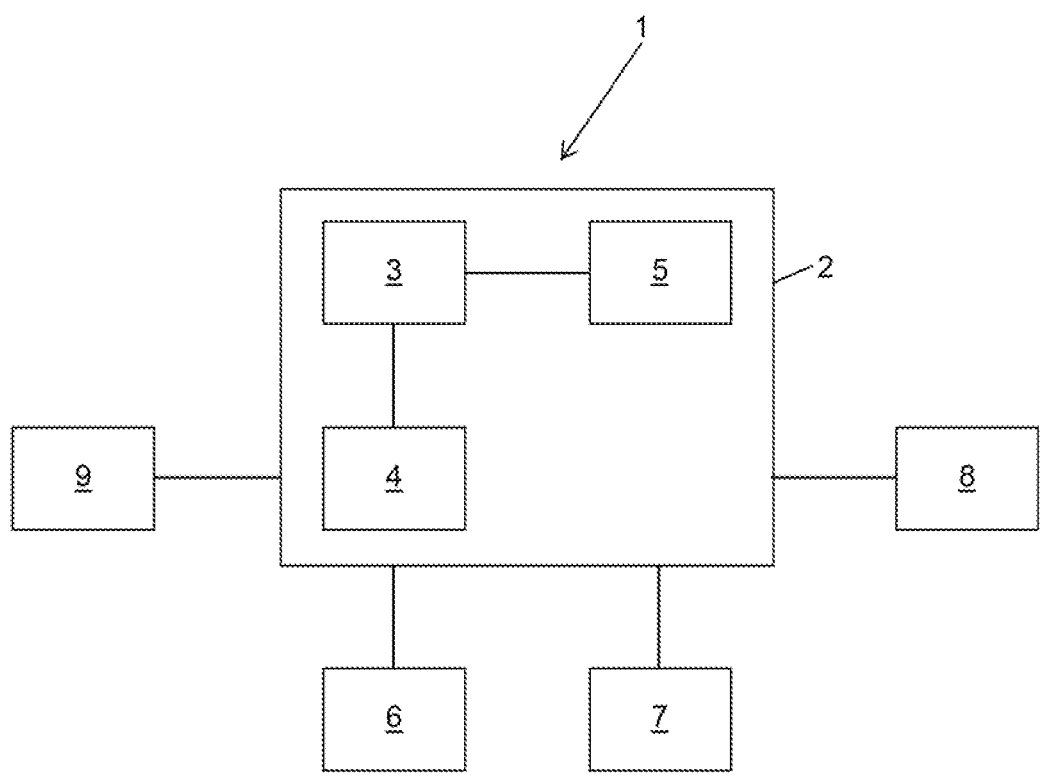

Sherbondy, ConTrack: Finding the most likely pathways between brain regions using diffusion tractography, Journal of Vision (2008) 8(9):15, 1-16.*
International Search Report and Written Opinion for International Application No. PCT/EP2012/065567 dated Apr. 18, 2013.
Sebastiano Barbieri et al., "Atlas-based fiber reconstruction from diffusion tensor MRI data", International Journal of Computer Assisted Radiology and Surgery; A Journal for Interdisciplinary Research, Development and Applications of Image Guided Diagnosis and Therapy, vol. 7, No. 6, Jun. 2012, pp. 959-967.
A.J. Sherbondy et al., "ConTrack: Finding the most likely pathways between brain regions using diffusion tractography", Journal of Vision, vol. 8, No. 9, Jul. 1, 2008, p. 15.
Cook et al., "Atlas-guided probabilistic diffusion-tensor fiber tractography", Biomedical Imaging: From Nano to Macro, May 2008, pp. 951-954.

* cited by examiner

LOCALIZATION OF FIBROUS NEURAL STRUCTURES

RELATED APPLICATION DATA

This application is a national phase application of International Application No. PCT/EP2012/065567 filed Aug. 9, 2012 and published in the English language.

The present invention relates to a data processing method for determining a path of a neural fibre in a patient, a computer program, a computer and a medical diagnostic system.

For many medical applications, knowledge about the location of neural fibres is advantageous or required. Known approaches are, for example, based on an MRE sequence called constructive interference in steady state (CISS), in particular for detecting nerves, or using techniques based on magnetic resonance imaging (MRI) in order to obtain diffusion directions, such as diffusion tensor imaging (DTI) or high angular resolution diffusion imaging (HARDI). However, these approaches can either not be automated or are not suitable for thin structures It is an object of the present invention to provide a data processing method for determining a path of a neural fibre in a patient even for thin fibres and in case of crossing or branching fibres, as well as a corresponding computer program, computer and medical diagnostic system. This is achieved by the subject-matter of the independent claims. Advantageous embodiments are defined in the dependent claims.

The method for determining a path of a neural fibre in a patient comprises a first step of acquiring an atlas dataset representing an atlas of a fibrous structure comprising the neural fibre and a second step of acquiring a nerve indicating dataset comprising information suitable for identifying the neural fibre in the patient. As will be explained below, the atlas is a generic representation of the fibrous structure comprising generic neural fibres, whereas the nerve indicating dataset relates to the particular patient and is determined from image data obtained using a suitable modality, such as diffusion tensor imaging (DTI) or constructive interference in steady state (CISS). The nerve indicating dataset is thus a DTI dataset or a CISS dataset, respectively. However, any imaging modality can be used as long as the resulting dataset allows to identify the neural fibre in the patient.

A third step of the method relates to calculating a matched atlas dataset by registering the atlas dataset with the nerve indicating dataset. In this step, the generic fibrous structure of the atlas is adapted to the anatomy of the patient. The registration can be performed using any suitable approach, such as rigid or elastic fusion.

A fourth step of the method relates to obtaining a generic path of the neural fibre from the matched atlas dataset. A generic neural fibre, being a counterpart of the neural fibre to be detected in the patient, is identified in the matched atlas dataset and then the corresponding generic path of the counterpart generic neural fibre in the matched atlas dataset is obtained, for example by simply copying the generic path. Since the atlas dataset is matched to the nerve indicating dataset, the generic path more or less resembles the sought-after path in the patient.

It shall be noted that the neural fibre, and therefore the path of the neural fibre, can simply connect two end points. However, in the case of a branched neural fibre in the shape of a Y, the path can have three end points. In the case of a crossing neural fibre in the shape of an X, the path can have four end points. Depending on the structure of the neural fibre, the path can even have more than four end points. Depending on the properties of the path to be determined, the obtained generic path can have less end points than the fibre in the atlas by ignoring parts of the fibre in the atlas.

A fifth step of the method relates to defining a constraining volume in the patient around the generic path, the constraining volume having at least two end surfaces on which the generic path ends. The number of end surfaces equals the number of end points of the generic path. Preferably, the end surfaces are orthogonal to the generic path. It is to be noted that the generic path may represent the complete neural fibre or only a part of the length of the neural fibre. If the generic path, and therefore sought-after path of the neural fibre in the patient, only corresponds to a part of the fibre, then this part is referred to as path or generic path.

A sixth step of the method relates to determining the path of the neural fibre between the end surfaces using a probabilistic approach, wherein the determined path lies completely within the constraining volume. Probabilistic approaches for determining a path of a neural fibre are well-known, and two examples will be described in detail below. The probabilistic approach, also referred to as probabilistic fibre tracking algorithm, can be based on any suitable and/or available imaging modality and is based on the nerve indicating dataset.

The present invention combines the effects of a pre-segmentation based on the atlas dataset for determining a constraining volume within which the path of the neural fibre is sought with a probabilistic fibre tracking algorithm. This means that the fibre tracking algorithm is constrained to a search volume which is defined on the basis of the atlas dataset. Compared to purely atlas-based approach, additional information present in the nerve indicating dataset is taken into account. Compared to a purely probabilistic fibre tracking algorithm, prior knowledge about the sought-after fibre is utilized.

Preferably, the constraining volume is tubular and centered about the generic path. In the case of a simple fibre, a constraining volume thus has a hose-shaped appearance. The end surfaces of the constraining volume might be squares, might be circles or might be ellipses. The size of the cross-sectional area of the constraining volume, and thus the size of the end surfaces if the constraining volume is considered to be constant in size over the whole length, preferably depends on the size of the neural fibre. In particular, the size means the diameter of a volume with circular end surfaces, the edge length of a volume having square end surfaces or one of the axes, in particular the longer axis, of a volume having elliptic end surfaces. Preferably, this size is 1 mm, 2 mm, 3 mm, 4 mm, 5 mm or 10 mm, for example. The length refers to the distance, along the generic path, of the constraining volume between two end surfaces. As an alternative, the size of the constraining volume can vary over the length of the constraining volume. The size of the constraining volume, or the course of the constraining volume over its length, can be defined in the atlas, for example for sections of the length. The size can for example be proportional to the diameter of a bundle of fibres to be detected.

As an option, the method comprises the step of acquiring input data which represents manually input amendments to the constraining volume. The constraining volume is then amended according to the input data. This may mean at least one of a shift of the generic path, a change of the size of the constraining volume, adding a region to the constraining volume or removing a region from the constraining volume.

The latter approach allows for excluding particular regions, such as regions occupied by a bone or another structure, from the constraining volume in which the fibre is searched for.

An atlas typically consists of a plurality of generic models of objects, wherein the generic models of the objects together form a complex structure. The atlas of a femur, for example, can comprise the head, the neck, the body, the greater trochanter, the lesser trochanter and the lower extremity as objects which make up the complete structure. The atlas of a brain, for example, can comprise the telencephalon, the cerebellum, the diencephalon, the pons, the mesencephalon and the medulla as the objects which make up the complex structure. An atlas of a fibrous structure comprises generic paths of neural fibres. The atlas can be derived from DTI image data, CISS data or data of any other suitable imaging modality. One application of such an atlas is in the segmentation of medical images, wherein the atlas is matched to medical image data, and the image data are compared with the matched atlas in order to assign a point (a pixel or voxel) of the image data to an object of the matched atlas, thereby segmenting the image data into objects.

In the field of medicine, imaging methods are used to generate image data (for example, two-dimensional or three-dimensional image data) of anatomical structures (such as soft tissues, bones, organs, etc.) of the human body. Medical imaging methods are understood to mean advantageously apparatus-based imaging methods (so-called medical imaging modalities and/or radiological imaging methods), such as for instance computed tomography (CT) and cone beam computed tomography (CBCT; in particular volumetric CBCT), x-ray tomography, magnetic resonance tomography (MRT or MRI), conventional x-ray, sonography and/or ultrasound examinations, and positron emission tomography. Analytical devices are in particular used to generate the image data in apparatus-based imaging methods. The imaging methods are in particular used for medical diagnostics, to analyse the anatomical body in order to generate images which are described by the image data.

The method in accordance with the invention is in particular a data processing method. The data processing method is preferably performed using technical means, in particular a computer. The data processing method is in particular executed by or on the computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing" which describes computation, software, data access and storage services which do not require the end user to know the physical location and/or configuration of the computer delivering a specific service. In particular, the term "cloud" is used as a metaphor for the internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer.

The expression "acquiring data" encompasses in particular (within the framework of a data processing method) the scenario in which the data are determined by the data processing method or program. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe which is preferably called "XY information".

Elastic fusion transformations (e.g. image fusion transformation) are in particular designed to enable a seamless transition from one data set (e.g. first data set, e.g. first image) to another data set (e.g. second data set, e.g. second image). The transformation is in particular designed such that one of the first and second data sets (images) is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are in particular vectors of a deformation field F. These vectors are determined by the optimisation algorithm which results in an optimum degree of similarity. Thus, the optimum degree of similarity represents a condition, in particular a constraint, for the optimisation algorithm. The bases of the vectors lie in particular at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), in particular in order to avoid pathological deformations (for instance, all the voxels being shifted to the same position by the transformation). The constraints include in particular the constraint that the transformation is regular, which in particular means that a Jacobian determinant calculated from a matrix of the deformation field (in particular, the vector field) is larger than zero. The constraints include in particular the constraint that the transformed (deformed) image is not self-intersecting and in particular that the transformed (deformed) image does not comprise faults and/or ruptures. The constraints include in particular the constraint that if a regular grid is transformed simultaneously with the image and in a corresponding manner, the grid is not allowed to interfold at any of its locations. The optimising problem is in particular solved iteratively, in particular by means of an optimisation algorithm which is in particular a first-order optimisation algorithm, in particular a gradient descent algorithm. Other examples of optimisation algorithms include optimisation algorithms which do not use derivations such as the downhill simplex algorithm or algorithms which use higher-order derivatives such as Newton-like algorithms. The optimisation algorithm preferably performs a local optimisation. If there are a plurality of local optima, global algorithms such as simulated annealing or genetic algorithms can be used. In the case of linear optimisation problems, the simplex method can for instance be used.

In the steps of the optimisation algorithms, the voxels are in particular shifted by a magnitude in a direction such that the degree of similarity is increased. This magnitude is preferably less than a predefined limit, for instance less than $\frac{1}{10}$ or $\frac{1}{100}$ or $\frac{1}{1000}$ of the diameter of the image, and in particular about equal to or less than the distance between neighbouring voxels. Due in particular to a high number of (iteration) steps, large deformations can be implemented.

The determined elastic fusion transformation can be in particular used to determine a degree of similarity (similarity measure also referred to as "measure of similarity") between the first and second data set (first and second image). To this end, the deviation of the elastic fusion transformation and an identity transformation is determined. The degree of deviations can be for instance calculated by determining the difference between the determinant of the elastic fusion transformation and the identity transformation. The higher the deviation is the less is the similarity. Thus, the degree of deviation can be used to determine a measure of similarity.

A measure of similarity can in particular be determined on the basis of a determined correlation between the first and second data set.

As indicated above, there are a plurality of probabilistic approaches for determining the path of the neural fibre. According to the present invention, these approaches are combined with a constraining volume in which the path has to lie. Two exemplary approaches shall be explained next.

A first approach of determining the path of the neural fibre comprises selecting a seed point on one of the end surfaces as a current point and calculating a path vector, the path vector having a length and direction and starting at the current point, from data of the nerve indicating dataset at the current point. The approach further comprises storing the current point as a point in the path of the neural fibre and using the end point, or tip, of the path vector as the current point. The approach returns to the path vector calculation step if the path vector does not end on or extend through another surface or stops if the path vector extends through any other end surface of the constraining volume.

In this first approach, the path is established from point to point. The nerve indicating dataset indicates a direction into which the nerve extends from the current point. For example, a tensor of DTI dataset at the current point indicates the direction of the fibre and therefore of the path. If there is no data for the current point, existing data of one or more surrounding points can be interpolated or extrapolated in order to calculate data at the current point.

In a typical case, the nerve indicating dataset does not comprise a particular direction of the neural fibre at the current point, but rather a probability distribution of the neural fibres direction, such as a Bingham distribution. The direction of the path vector is stochastically calculated based on the directional distribution. Preferably, the length of the path vector is also determined based on the directional distribution, for example being proportional to the inverse of the probability of the direction of the path vector. If the end point of the path vector lies within the constraining volume, then this end point is used as the new current point and a new path vector is calculated for this current point, such that the path is iteratively established. If the end point of the path vector lies on an end surface of the constraining volume other than the end surface on which the seat point of the path lies, then a valid path has been found. The endpoint of the path vector lying the outside the constraining volume can have two different causes. In the first case, the path vector extends through an end surface other than the end surface comprising the seed point. In this case, a valid path has been found. In the second case, the path vector extends through any other surface of the constraining volume. In this case, a part of the path lies outside the constraining volume such that path determination is stopped and the path is discarded.

A second approach of determining the path of the neural fibre comprises selecting a sequence of points for which data exist in the nerve indicating dataset, wherein the number of points in the sequence is below a predetermined number of points, the start point and the end point of the sequence are located on or behind end surfaces and all other points are located within the constraining volume. In other words, an arbitrary chain of points within the constraining volume and connecting two end surfaces of the constraining volume is established. In this approach, only points are used for which data exists in the nerve indicating dataset, which in the case of DTI dataset means that a diffusion tensor exists for the point. In addition, the number of points is limited, for example depending on the length of the generic path. Preferably, the number of points in the sequence is limited to 1, 2, 5, 10 or 20 points per 10 mm length of the generic path. This approach is explained in detail in the article "ConTrack: Finding the most likely pathways between brain regions using diffusion tractography" by Anthony J. Sherbondy et al., published in Journal of Vision (2008) 8(9):15, 1-6, the entire contents of which are hereby incorporated herein by reference.

With the approach of selecting only points for which data exists in the nerve indicating dataset, it is likely that at least one of the start point and the end point of the sequence is not located on an end surface of the constraining volume. The start point and/or end point of the sequence may therefore also be located behind an end surface of the constraining volume. This means that the line connecting the start point or end point, respectively, with its neighbouring point in the sequence or chain of points extends through an end surface of the constraining volume, but not through any other surface of the constraining volume.

With the second approach, an arbitrary path lying completely within the constraining volume can be established. The only influence the nerve indicating dataset has on the path is that the points of the path have to correspond to sampling points of data in the nerve indicating dataset. However, an optional constraint is that the distance of two consecutive points in the sequence is below a predetermined distance threshold, such as 1 mm, 2 mm or 5 mm.

It is to be noted that, in both approaches for determining the path of the neural fibre, the path is considered to lie completely within the constraining volume even if the start point/seed point or the end point of the path lies outside the constraining volume. In this case, the path might be cut at an end surface through which the path extends.

If the neural fibre the path of which has to be determined has more than two end points, then the constraining volume has more than two end surfaces. In this case the path connects a first end surface with more than one second end surface. In the step of determining the path of the neural fibre between end surfaces, an appropriate number of branches of the path is introduced, for example at random points of the path or preferably at a point close to the corresponding branch in the generic path. In particular, the branch is introduced at the last point of the path before the corresponding branch in the generic path.

As an option, the acquired input data represents a position of at least one start/seed point and/or at least one end point of the path. The input data may represent the exact position of a point, a region in which the point lies or a region in which a point mustn't lie.

In a preferred embodiment, a plurality of paths is determined by repeating the sixth step of the method, that is the step of determining the path of the neural fibre between the end surfaces using a probabilistic approach. Since the approach for determining the path is probabilistic, this results in a plurality of different paths, all lying within the constraining volume. Preferably, a score is assigned to each of the determined paths. Further preferably, all paths with a score below a predetermined score threshold are discarded. The predetermined score threshold is for example set such that a predetermined percentage, such as 5, 10, 15, 20 or 25 percent, or a predetermined number of paths, such as 100, 200, 500 or 1000 paths, remains. The number of determined paths may be 100000, 1000000, 2000000, 5000000 or 10000000. Preferably, a plurality of start points or seed points is used for determining the paths. Further preferably, the start points/seed points are uniformly distributed on the end surface or behind the end surface, or on or behind more than one end surface. For example, half of the paths is determined starting from a first end surface and the other half of the paths is determined starting from another end surface. In this embodiment, each path can be considered as representing the path of a fibre in a bundle of fibres. This means that a fibre bundle can be detected.

In one embodiment, the score is calculated depending the nerve indicating dataset. Since the nerve indicating dataset comprises information about the path of the neural fibre, the similarity between a particular path and the corresponding data in the nerve indicating dataset can be calculated. In the case of a DTI dataset, the score is calculated based on the diffusion tensors of the points making up the path. In case of the first approach for determining the path of the neural fibre, one possible implementation is to calculate a score for each point based on the probability for the path vector pointing in its chosen direction, wherein the probability relates to the directional distribution in this point. The score is then determined from the average of the probabilities for the points (except for the end point) making up the path.

In case of the second approach for determining the path of the neural fibre, the directional distribution is also used to determine the probability with which the path continues in the direction of the next point in the sequence. As for the first approach, the probabilities are averaged over all points (except for the end point) of the sequence to determine the score.

In addition or as an alternative, the score is calculated depending on a path property dataset representing information about known properties of the neural fibre. The path property dataset represents how well a path can be explained by prior knowledge, such as assumptions about smoothness, direction or curvature of the path. The path property dataset may represent that sharp turns in the path of a neural fibre are very unlikely, strong deviations from the direction of the generic path are very unlikely or some neural fibres have a very specific curvature pattern and/or curve in only one direction. Preferably, an overall score is calculated depending on both the nerve indicating dataset and the path property dataset, for example by averaging the two parts of the score.

In one embodiment, the score represents the probability that the corresponding path is the correct path. This probability is given as p(P|D), wherein P stands for the path and D for the nerve indicating dataset. p(P|D) is the probability that P is the correct path under the condition that the nerve indicating dataset D is given. According to the Bayes rule, p(P|D)=p(D|P)*p(P). This shows that the score has a component p(D|P) which depends on the nerve indicating dataset and a component p(P) which does not depend on the nerve indicating dataset, but on the path property dataset.

Preferably, each of the probabilities p(D|P) and p(P) is established from partial probabilities for each of the points of the respective path. In particular, p(D|P) is the product of the partial probabilities $p_i(D|P)$ and p(P) is the product of the partial probabilities $p_i(P)$, wherein i is the index for the points in the path P. In an alternative, the logarithms of the partial probabilities can be summed up instead of multiplying the partial probabilities.

The step of calculating a matched atlas dataset can be performed by directly registering the atlas dataset with the nerve indicating dataset, in particular if both datasets comprise corresponding references, such as landmarks, which can be used for the registration. However, another approach for registering comprises a plurality of steps.

In a first step, the atlas dataset is registered with an intermediate modality atlas dataset in order to obtain an intermediate atlas dataset. As outlined above, the atlas dataset is determined using a suitable modality such as DTI or CISS. An atlas is typically created by merging a plurality of samples of the same structure from different sample objects, such as sample bodies. The segmentation into the generic models of objects, in the present case of paths of neural fibres, is typically performed manually by an expert. The intermediate modality is a modality which is used in order to image the body of a patient. Typical intermediate modalities are CT or MRI. The intermediate modality atlas dataset therefore corresponds to a modality different from the modality used for preparing the atlas dataset, but relating to the same (generic) structure as the atlas dataset. This means that the first step relates to an intra-subject registration.

In a second step, the intermediate modality atlas dataset is registered with an intermediate modality patient dataset to obtain a first transformation rule. The intermediate modality atlas dataset and the intermediate modality patient dataset relate to the same intermediate modality. This step therefore relates to an inter-subject registration.

In a third step, the intermediate modality patient dataset is registered with the nerve indicating dataset to obtain a second transformation rule. In this step, the intermediate modality patient dataset and the nerve indicating dataset, which both refer to a particular patient, are registered with each other in an intra-subject registration. The intermediate modality patient dataset and the nerve indicating dataset are preferably created during the same imaging session. In particular, imaging runs for creating the intermediate modality patient dataset and the nerve indicating dataset are performed intermittently.

In a fifth step, the intermediate atlas dataset is matched to the nerve indicating dataset using the first and second transformation rules. With this approach of calculating the matched atlas dataset, the intermediate modality datasets are used in order to obtain a transformation rule comprised of the first transformation rule and the second transformation rule which is then used to register the intermediate atlas dataset with the nerve indicating dataset.

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (in particular on the surface of) a characteristic anatomical structure of the body part can also represent said structure. The landmark can represent the anatomical structure as a whole or only a point or part of it. A landmark can also for example lie on the anatomical structure, which is in particular a prominent structure. An example of such an anatomical structure is the posterior aspect of the iliac crest. Other landmarks include a landmark defined by the rim of the acetabulum, for instance by the centre of the rim. In another example, a landmark represents the bottom or deepest point of an acetabulum, which is derived from a multitude of detection points. Thus, one landmark can in particular represent a multitude of detection points. As mentioned above, a landmark can represent an anatomical characteristic which is defined on the basis of a characteristic structure of the body part. Additionally, a landmark can also represent an anatomical characteristic defined by a relative movement of two body parts, such as the rotational centre of the femur when moved relative to the acetabulum.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements and optionally a volatile memory (in particular, a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The present invention further relates to a medical diagnostic system comprising a computer as described above and an interface for acquiring at least the atlas dataset and the nerve indicating dataset. Via the interface, the medical diagnostic system can be connected to a data storage medium comprising a dataset or a medical imaging apparatus which generates the dataset. The medical diagnostic system may be connected to more than one imaging apparatus or to at least one data storage medium and at least one imaging apparatus. The data storage medium or media and/or the image apparatus may be a part of the medical diagnostic system.

It lies within the scope of the present invention to combine one or more features of embodiments, examples, approaches or options to form a new embodiment, example, approach or option as long as technically feasible.

Figure 2:
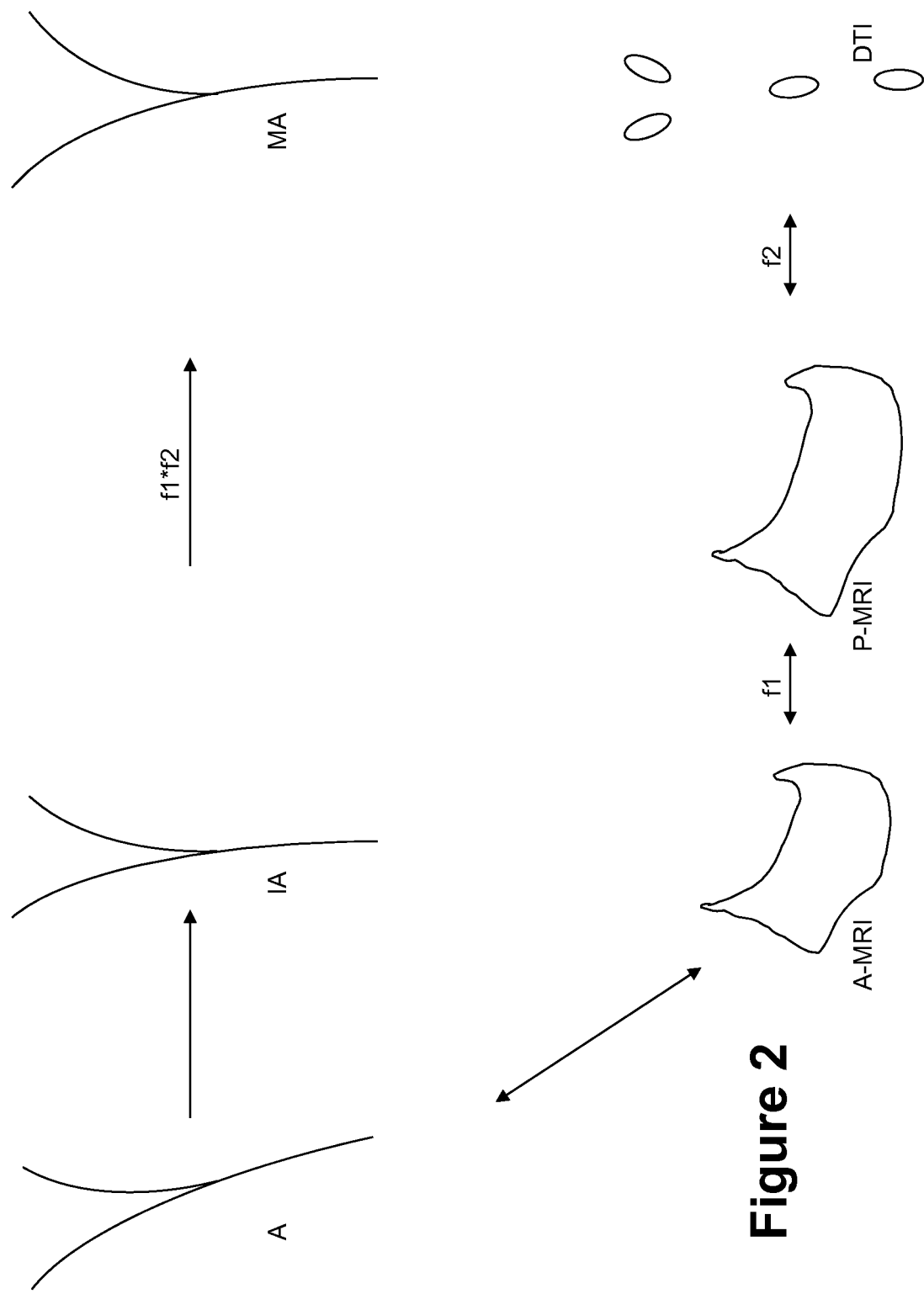
Figure 3:
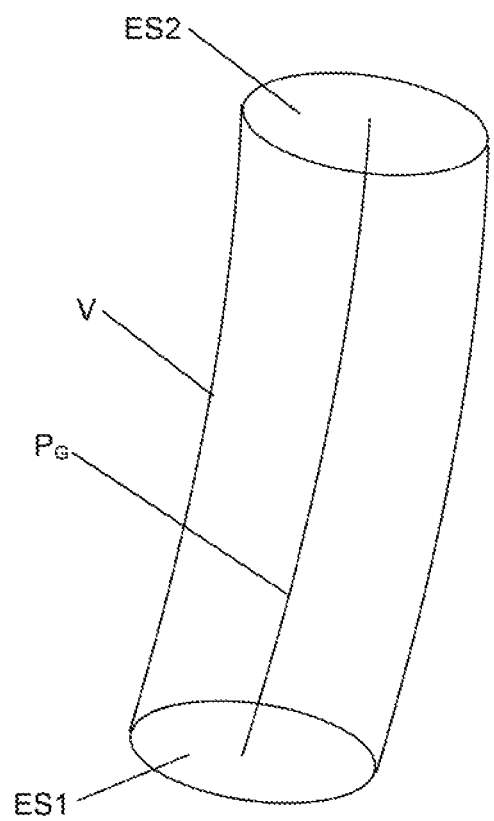
Figure 4:
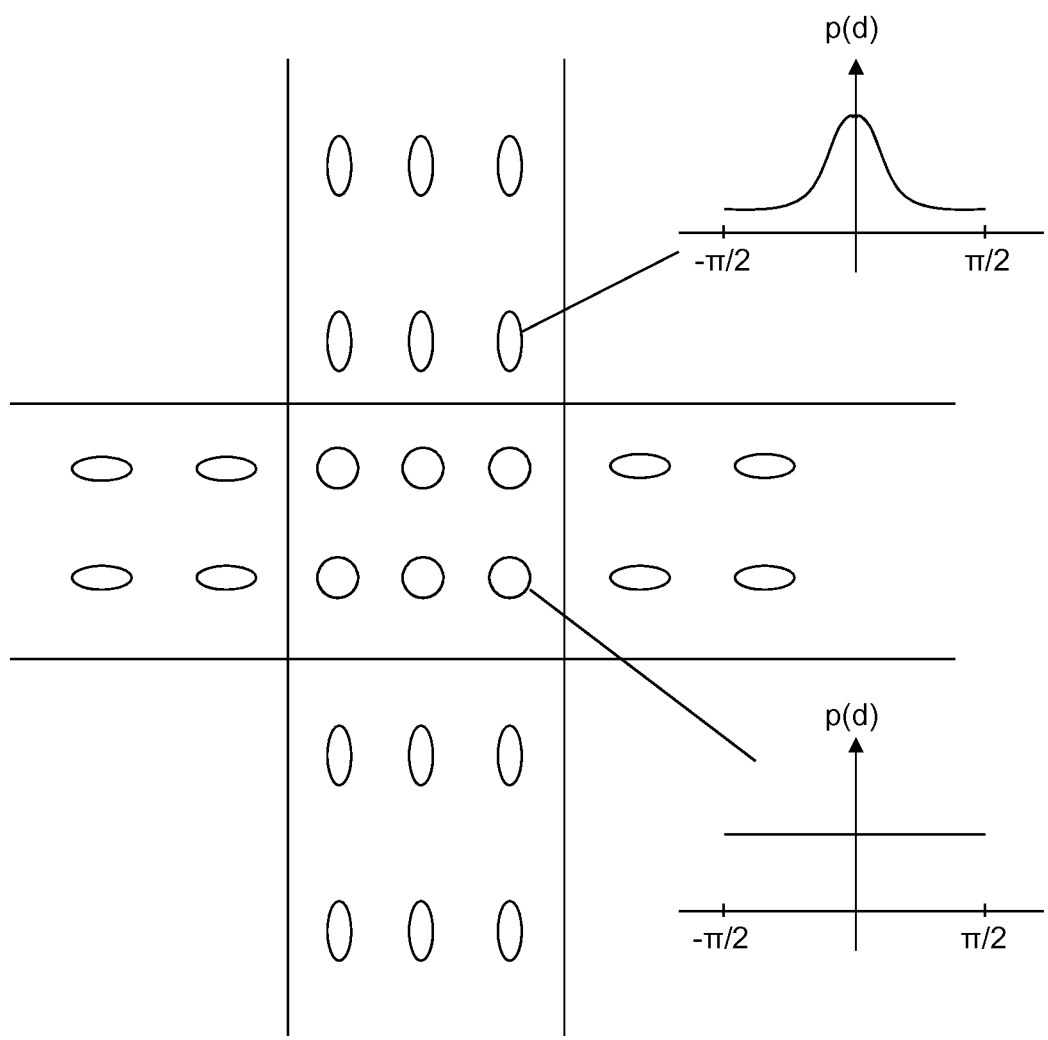
Figure 5:
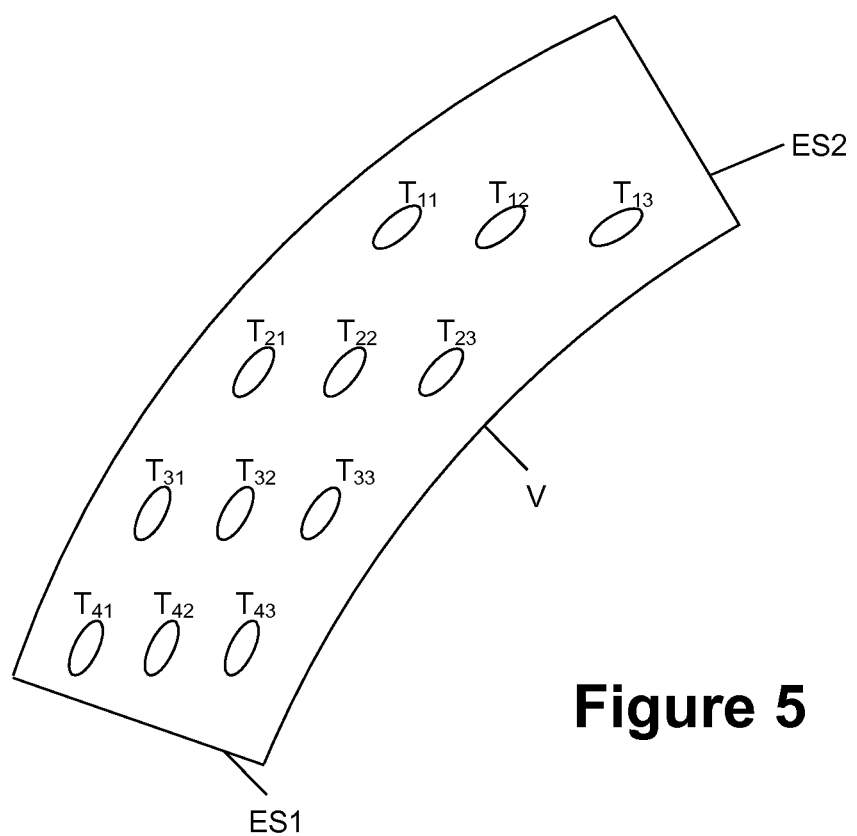
Figure 6:
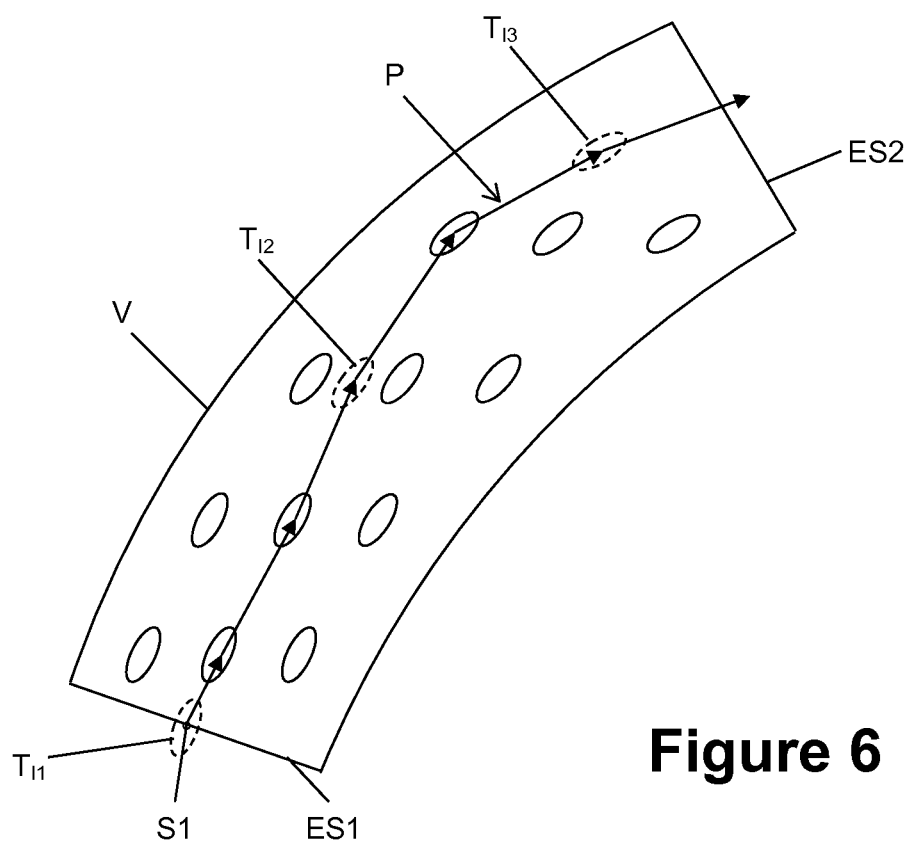
Figure 7:
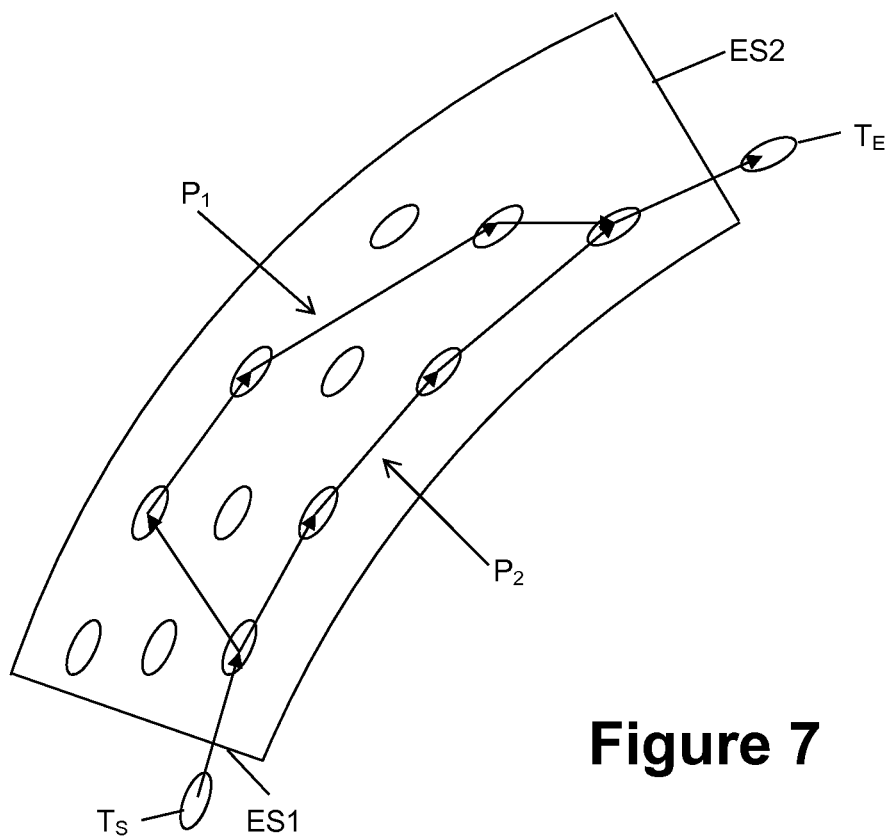

The present invention shall be explained in more detail with reference to the accompanying Figures. These Figures show:

FIG. 1 a medical diagnostic system
FIG. 2 matching an atlas to DTI data
FIG. 3 a constraining volume around a generic fibre
FIG. 4 DTI tensors for crossing fibres
FIG. 5 DTI tensors within a constraining volume
FIG. 6 a first approach for determining a path through the constraining volume and
FIG. 7 a second approach for determining a path through the constraining volume.

FIG. 1 shows a medical diagnostic system 1 for performing a data processing method for determining a path of a neural fibre in a patient. The medical diagnostic system 1 comprises a computer 2 connected to an input device 6, such as a keyboard, a mouse or a touch screen, and an output device 7, such as a monitor or any other display device. The computer 2 is further connected to a storage device 8 and an MRI imaging apparatus 9. The computer 2 comprises a central processing unit 3, and interface 4 and a memory 5. The computer 2 is connected to the storage 8 and the imaging apparatus 9 via the interface 4. The central processing unit 3 performs the method described herein using data acquired from the imaging apparatus 9 and/or the storage 8. The program for performing the method is stored in memory 5. Optionally further stored in the memory 5 are data acquired from the imaging apparatus 9 and/or the storage 8.

The computer first acquires an atlas dataset representing an atlas of a fibrous structure comprising the neural fibre and a diffusion tensor imaging (DTI) dataset as an example of a nerve indicating dataset comprising information suitable for identifying the neural fibre in the patient. The central processing unit 3 then calculates a matched atlas dataset by registering the atlas dataset with the DTI dataset. This is shown in detail in FIG. 2. In its upper left, FIG. 2 shows an atlas dataset A, which in the present exemplary embodiment only represents a single neural fibre having a branching structure, such that the path of the neural fibre has the shape of an Y.

The computer 2 also acquires an intermediate modality atlas dataset and an intermediate modality patient dataset. In the present embodiment, the intermediate modality is MRI. The intermediate modality atlas dataset, referred to as A-MRI in FIG. 2, represents MRI data corresponding to the same (generic) structure or body as the atlas A. The intermediate modality patient dataset, referred to in FIG. 2 as P-MRI, refers to the same patient as the DTI dataset.

In a first step, the atlas dataset A is registered with the MRI atlas dataset A-MRI in order to obtain an intermediate atlas dataset IA. The intermediate atlas dataset IA is thus aligned with the MRI atlas dataset A-MRI. As an alternative, the atlas dataset can already be registered with the MRI atlas dataset.

In a second step, the MRI atlas dataset A-MRI is registered with the MRI patient dataset P-MRI in order to obtain a first transformation rule f1 which maps the MRI atlas dataset to the MRI patient dataset. In a third step, the MRI patient dataset P-MRI is registered with the DTI dataset in order to obtain a second transformation rule f2. This second transformation rule f2 maps the MRI patient dataset to the DTI dataset. By combining the first transformation rule f1 and the second transformation rule f2, the intermediate atlas dataset IA can be directly mapped to the DTI dataset, resulting in a matched atlas dataset MA. In other words, the atlas is now mapped to the status of the patient as represented by the DTI dataset. In particular, the atlas dataset A is mapped into a reference or coordinate system of the patient. The matched atlas dataset then represents an approximation of the fibrous structure in the patient.

The central processing unit 3 then obtains a generic path $P_G$ of the neural fibre from the matched atlas dataset MA. In this exemplary embodiment, the generic path $P_G$ shown in FIG. 3 represents only a part of the full length of the neural fibre. In this example, the generic path $P_G$ is simply copied from the matched atlas dataset MA.

The central processing unit 3 then defines a constraining volume in the patient around the generic path $P_G$. The constraining volume is labeled V in FIG. 3. The constraining volume V has at least two end surfaces on which the generic path ends. If neural fibre continues outside the constraining volume V, then only the part of the neural fibre inside the constraining volume V is represented by the generic path $P_G$ in this document.

FIG. 4 shows a part of a DTI dataset for two crossing neural fibres. Diffusion tensors of the DTI are represented by circles and ellipses. The shape of the representation of a tensor indicates the directional distribution of the tensor, such as a Bingham distribution. In general, the directional distribution is three-dimensional. For a particular direction, the directional distribution provides the probability with which the neural fibre runs in this particular direction.

For simplifying the illustration, the directional distribution is depicted in two dimensions in FIG. 4. Along a single fibre, the tensor typically represents a preferred direction, resulting in a probability distribution of the directions having a clear maximum. In the upper graph in FIG. 4, the probability p(d) for a particular direction d of the neural fibre is plotted over the direction d, given as an angle between $-\pi/2$ and $\pi/2$. In an area where the two neural fibres are crossing, the tensor is represented by a circle because the tensors do not provide a preferred direction. Instead, the probability p(d) is uniformly distributed over the whole range from $-\pi/2$ to $\pi/2$. In this area, a fibre tracking algorithm based on DTI data will probably fail.

FIG. 5 shows a sectional view through the constraining volume V having two end surfaces ES1 and ES2 together with a part of the DTI dataset. In particular, twelve tensors of the DTI dataset are shown. The tensors are denoted by T in combination with a two-digit index. In the representation shown in FIG. 5, the first digit of the index represents the row and the second digit of the index represents the column of a tensor T. The central processing unit 3 then determines the path of the neural fibre between the end surfaces ES 1 and ES2 using a probabilistic approach, wherein the determined path lies completely within the constraining volume V. Two approaches for determining the path of the neural fibre are explained with reference to FIGS. 6 and 7 which are based on the constraining volume V and the diffusion tensors shown in FIG. 5.

The first explained with reference to FIG. 6 starts with a starting point S1 on an end surface S1 of the constraining volume V. Since the DTI dataset does not comprise a tensor at this point S1, the central processing unit 3 interpolates other tensors, resulting in an interpolated tensor $T_{I1}$. From the directional distribution corresponding to the interpolated tensor $T_{I1}$, the central processing unit 3 calculates a path vector having a random direction. The length of a path vector can be constant, inversely proportional to the probability of the direction of the path vector or calculated using another probability distribution. In the present example, the end point of the path vector starting at the point S1 is the point, or location, of the tensor $T_{42}$. The CPU 3 then calculates a new path vector starting at the point of the tensor $T_{42}$ based on the directional distribution represented by the tensor $T_{42}$. The endpoint of this path vector is the point, or location, of the tensor $T_{32}$.

In analogy, the central processing unit 3 calculates a new path vector. The end point of this new path vector does not coincide with a point, or location, of a tensor in the DTI dataset. The central processing unit 3 therefore interpolates a tensor $T_{I2}$ from surrounding tensors of the DTI dataset and calculates a new path vector, the end point of which coincides with the point, or location, of the tensor $T_{11}$. The central processing unit 3 then calculates a new path vector from the tensor $T_{11}$ and starting at its location.

This new path vector ends at a point for which no tensor exists in the DTI data, such that the central processing unit 3 interpolates a new tensor $T_{I3}$. The central processing unit 3 then calculates a new path vector as described above. This new path vector extends through the opposite end surface ES2 of the constraining volume V. The central processing unit has thus found a valid path between the end surfaces ES1 and ES2. This path completely lies within the constraining volume V and is represented by the point S1, the locations of the tensors $T_{I1}$, $T_{32}$, $T_{I2}$, $T_{11}$ and $T_{I3}$ as well as the point at which the last path vector intersects with the end surface ES2.

As a preferred option, plurality of paths of the neural fibre between the end surfaces ES1 and ES2 is determined. For the same starting point S1, the paths will be different because the directions of the path vectors are calculated based on a directional distribution using a probabilistic approach. In addition, a plurality of start points on the first end surface ES1 can be used.

A second approach for determining the path of the neural fibre is explained with reference to FIG. 7. This approach comprises selecting a sequence of points for which diffusion tensors exist in the DTI dataset. The start point and the end point of the sequence are located on or behind the end surfaces ES1 and ES2 and all other points are located within the constraining volume V.

As can be seen from FIG. 7, there are no tensors in the DTI dataset for points lying on the end surfaces ES1 and ES2. The central processing unit 3 therefore uses points, or locations, of tensors $T_S$ and $T_E$ located behind the end surfaces ES1 and ES2, respectively, as start and end points of the sequence. A point is considered as lying behind an end surface if the straight connection between this point and the neighbouring point in the sequence passes through the end surface, but no other surface of the constraining volume V.

The central processing unit 3 determines a first path $P_1$ of the neural fibre as the sequence of points, or locations, of the tensors $T_S$, $T_{43}$, $T_{31}$, $T_{21}$, $T_{12}$, $T_{13}$ and $T_E$. Preferably, the central processing unit 3 determines a plurality of paths, for example including a second path $P_2$ of the neural fibre comprising the sequence of points, or locations, of the tensors $T_S$, $T_{43}$, $T_{33}$, $T_{23}$, $T_{13}$ and $T_E$.

Preferably, in particular if a plurality of paths is determined, each path is assigned a score. Preferably, the score represents the likelihood that the corresponding path is the correct path of the neural fibre in the patient. The score has at least one of a data dependent part depending on the DTI dataset and a data independent part depending on a path property dataset representing information about known properties of the neural fibre.

As explained with reference to FIGS. 6 and 7, the directions of the path vectors forming the path have a certain probability depending on the directional distribution corresponding to the tensors at the starting points of the respective path vectors. Preferably, the data dependent part of the score is calculated as the average of the probability of the selected path vector directions.

This shall be explained with reference to the paths $P_1$ and $P_2$ shown in FIG. 7. The first path $P_1$ branches from the point, or location, of the tensor $T_{43}$ to the point, or location, of the tensor $T_{31}$, while the path $P_2$ branches to the point, or location, of the tensor $T_{33}$. It is assumed that the directional distribution corresponding to the tensor $T_{43}$ is the one shown in the upper graph in FIG. 4. This means that the probability for the path vector starting at the point, or location, of the tensor $T_{43}$ pointing to the point of the tensor $T_{33}$ is significantly higher than the one pointing to the point of the tensor $T_{31}$. In analogy, all other path vectors are analyzed. As a result, the score of the path $P_2$ is higher than the score of the path $P_1$.

Several information about known properties of the neural fibre can be used for the data independent part of the score. For the neural fibre of this exemplary embodiment, it is known that it has a prevalent curvature to the right. Starting at the point, or location, of the tensor $T_{43}$, path $P_2$ continues to the right, while $P_1$ proceeds to the left. This results in a higher data independent part of the score for $P_2$ than for $P_1$.

Another known property of the particular neural fibre of the present exemplary embodiment is that sharp turns of the path are very unlikely. However, the path $P_1$ branching from the point of the tensor $T_{43}$ to the point of the tensor $T_{31}$ has a strong directional change relative to the incoming path vector compared to a significantly smaller directional change for the path vector of the path $P_2$ pointing to the point of the tensor $T_{33}$. Based on the known property of the smoothness of the neural fibre, path $P_1$ has a lower data independent part of the score than path $P_2$.

The invention claimed is:

1. A method for determining a path of a neural fibre in a patient, comprising the steps of:

a) acquiring an atlas dataset representing an atlas of a fibrous structure comprising the neural fibre;
b) acquiring a nerve indicating dataset comprising information corresponding to the patient and suitable for identifying the neural fibre in the patient;
c) calculating a matched atlas dataset by registering the atlas dataset with the nerve indicating dataset;
d) obtaining a generic path of the neural fibre from the matched atlas dataset;
e) defining a constraining volume in the patient around the generic path, the constraining volume having at least two end surfaces on which the generic path ends and the constraining volume is tubular and centered about the generic path; and
f) determining the path of the neural fibre between end surfaces of the constraining volume by:
selecting a seed point on one of the end surfaces as a current point;
iteratively calculating a path of the neural fibre until the path ends on or extends through another surface of the constraining volume, wherein for the current point, each iteration includes:
storing the current point as a point on the path of the neural fibre;
calculating a path vector starting from the current point and having a length and a direction based on data from the nerve indicating dataset corresponding to the current point; and
using an end point of the path vector as the current point in a next iteration; and
outputting the iteratively determined path of the neural fibre only when the path ends on or extends through an end surface of the constraining volume.

2. The method according to claim 1, wherein the nerve indicating dataset is a diffusion tensor imaging dataset or a constructive interference in steady state dataset.

3. The method according to claim 1, wherein a plurality of paths is determined by repeating step f).

4. The method according to claim 3, further comprising the step of assigning a score to each of the determined paths.

5. The method according to claim 4, comprising the step of discarding all paths with a score below a predetermined score threshold.

6. The method according to claim 4, wherein the score is calculated depending on the nerve indicating dataset.

7. The method according to claim 4, wherein the score is calculated depending on a path property dataset representing information about known properties of the neural fibre.

8. The method according to claim 1, wherein calculating the matched atlas dataset in step c) comprises registering the atlas dataset with an intermediate modality atlas dataset to obtain an intermediate atlas dataset, registering the intermediate modality atlas dataset with an intermediate modality patient dataset to obtain a first transformation rule, registering the intermediate modality patient dataset with the nerve indicating dataset to obtain a second transformation rule and matching the intermediate atlas dataset to the nerve indicating dataset using the first and second transformation rules.

9. A method for determining a path of a neural fibre in a patient, comprising the steps of:
a) acquiring an atlas dataset representing an atlas of a fibrous structure comprising the neural fibre;
b) acquiring a nerve indicating dataset comprising information corresponding to the patient and suitable for identifying the neural fibre in the patient;
c) calculating a matched atlas dataset by registering the atlas dataset with the nerve indicating dataset;
d) obtaining a generic path of the neural fibre from the matched atlas dataset;
e) defining a constraining volume in the patient around the generic path, the constraining volume having at least two end surfaces on which the generic path ends and the constraining volume is tubular and centered about the generic path; and
f) determining the path of the neural fibre between end surfaces of the constraining volume by:
selecting a sequence of points for which data exist in the nerve indicating dataset, wherein the number of points in the sequence is below a predetermined number of points, the start point and the endpoint of the sequence are located on or behind end surfaces and all other points are located within the constraining volume.

10. The method according to claim 9, wherein the distance of two consecutive points in the sequence is below a predetermined distance threshold.

11. The method according to claim 9, wherein a plurality of paths is determined by repeating step f).

12. The method according to claim 11, further comprising the step of assigning a score to each of the determined paths.

13. The method according to claim 12, comprising the step of discarding all paths with a score below a predetermined score threshold.

14. The method according to claim 12, wherein the score is calculated depending on the nerve indicating dataset.

15. The method according to claim 12, wherein the score is calculated depending on a path property dataset representing information about known properties of the neural fibre.

16. The method according to claim 9, wherein calculating the matched atlas dataset in step c) comprises registering the atlas dataset with an intermediate modality atlas dataset to obtain an intermediate atlas dataset, registering the intermediate modality atlas dataset with an intermediate modality patient dataset to obtain a first transformation rule, registering the intermediate modality patient dataset with the nerve indicating dataset to obtain a second transformation rule and matching the intermediate atlas dataset to the nerve indicating dataset using the first and second transformation rules.

17. A computer program embodied on a non-transitory computer readable medium which, when running on a computer or when loaded onto a computer, causes the computer to perform a data processing method for determining a path of a neural fibre in a patient, comprising the steps of:
a) acquiring an atlas dataset representing an atlas of a fibrous structure comprising the neural fibre;
b) acquiring a nerve indicating dataset comprising information corresponding to the patient and suitable for identifying the neural fibre in the patient;
c) calculating a matched atlas dataset by registering the atlas dataset with the nerve indicating dataset;
d) obtaining a generic path of the neural fibre from the matched atlas dataset;
e) defining a constraining volume in the patient around the generic path, the constraining volume having at least two end surfaces on which the generic path ends and the constraining volume is tubular and centered about the generic path; and
f) determining the path of the neural fibre between end surfaces of the constraining volume by:

selecting a seed point on one of the end surfaces as a current point;

iteratively calculating a path of the neural fibre until the path ends on or extends through another surface of the constraining volume, wherein for the current point, each iteration includes:

storing the current point as a point on the path of the neural fibre;

calculating a path vector starting from the current point and having a length and a direction based on data from the nerve indicating dataset corresponding to the current point; and using an end point of the path vector as the current point in a next iteration; and outputting the iteratively determined path of the neural fibre only when the path ends on or extends through an end surface of the constraining volume.

18. A computer program embodied on a non-transitory computer readable medium which, when running on a computer or when loaded onto a computer, causes the computer to perform a data processing method for determining a path of a neural fibre in a patient, comprising the steps of:

a) acquiring an atlas dataset representing an atlas of a fibrous structure comprising the neural fibre;
b) acquiring a nerve indicating dataset comprising information corresponding to the patient and suitable for identifying the neural fibre in the patient;
c) calculating a matched atlas dataset by registering the atlas dataset with the nerve indicating dataset;
d) obtaining a generic path of the neural fibre from the matched atlas dataset;
e) defining a constraining volume in the patient around the generic path, the constraining volume having at least two end surfaces on which the generic path ends and the constraining volume is tubular and centered about the generic path; and
f) determining the path of the neural fibre between end surfaces of the constraining volume by:
    selecting a sequence of points for which data exist in the nerve indicating dataset, wherein the number of points in the sequence is below a predetermined number of points, the start point and the endpoint of the sequence are located on or behind end surfaces and all other points are located within the constraining volume.

* * * * *